United States Patent [19]
Ferguson

[11] Patent Number: 6,095,323
[45] Date of Patent: Aug. 1, 2000

[54] SUTURE-MATERIAL-DISPENSER SYSTEM FOR SUTURE MATERIAL

[76] Inventor: Patrick J. Ferguson, P.O. Box 6724, Portland, Oreg. 97208

[21] Appl. No.: 09/097,304

[22] Filed: Jun. 12, 1998

[51] Int. Cl.[7] .................................................. B65H 47/00
[52] U.S. Cl. ........................................... 206/63.3; 206/204
[58] Field of Search ................................. 206/63.3, 63.5, 206/227, 380, 204, 368; 225/39, 46, 47

[56] References Cited

U.S. PATENT DOCUMENTS

| | | | |
|---|---|---|---|
| 418,271 | 12/1889 | Buckmaster | 206/63.3 |
| 693,138 | 2/1902 | Johnson | 206/63.3 |
| 2,128,701 | 8/1938 | Gelinsky . | |
| 2,808,927 | 10/1957 | Utley et al. . | |
| 3,382,141 | 5/1968 | Arledter et al. . | |
| 3,728,839 | 4/1973 | Glick . | |
| 3,815,315 | 6/1974 | Glick . | |
| 4,412,617 | 11/1983 | Cerwin . | |
| 4,519,501 | 5/1985 | Cerwin . | |
| 4,566,606 | 1/1986 | Kling . | |
| 4,606,134 | 8/1986 | Flick . | |
| 4,730,726 | 3/1988 | Holzwarth . | |
| 4,903,826 | 2/1990 | Pearce . | |
| 4,925,073 | 5/1990 | Tarrson et al. . | |
| 5,022,577 | 6/1991 | Fike . | |
| 5,065,861 | 11/1991 | Greene et al. . | |
| 5,086,914 | 2/1992 | Mish et al. . | |
| 5,133,747 | 7/1992 | Feaster . | |
| 5,160,077 | 11/1992 | Sticklin . | |
| 5,263,585 | 11/1993 | Lawhon et al. . | |
| 5,263,621 | 11/1993 | Bedi . | |
| 5,280,741 | 1/1994 | Bell et al. . | |

*Primary Examiner*—Jim Foster
*Attorney, Agent, or Firm*—Kolisch, Hartwell, Dickinson, McCormack & Heuser

[57] ABSTRACT

A suture-material-dispenser system for a supply of dry suture material includes the supply of such material, a housing which defines a cavity for containing the supply, and desiccant preferably housed within the housing. The housing includes a top region that has an opening formed in it, and a bottom region with a semi-circular bearing positioned in it. A reel fits within the cavity on the bearing, and has wound on it the supply. An anti-contaminant, flip-top cover is pivotably attached to the top region, and is constructed for releasable closure over the top region substantially to prevent contaminants from entering the cavity. A gas-permeable, resilient member is also included and has a body that fits sealingly within the opening, which body has formed in it a suture-material-dispensing port to allow dispensing of suture material therethrough. The body is preferably formed from a substance with a hardness in the range of about 40–80 on a Shore A durometer. An on-board cutter is also attached to the housing adjacent the resilient member for allowing the user to cut a desired dispensed amount of material from such supply. The cover may also include a downwardly extending, elongate pressure applicator with a bottom surface that presses against the resilient member adjacent the port when the cover is closed over the top region. Preferably, the resilient member is formed from a material that is ethylene-oxide-gas permeable, such as liquid-injection-molded silicone.

18 Claims, 4 Drawing Sheets

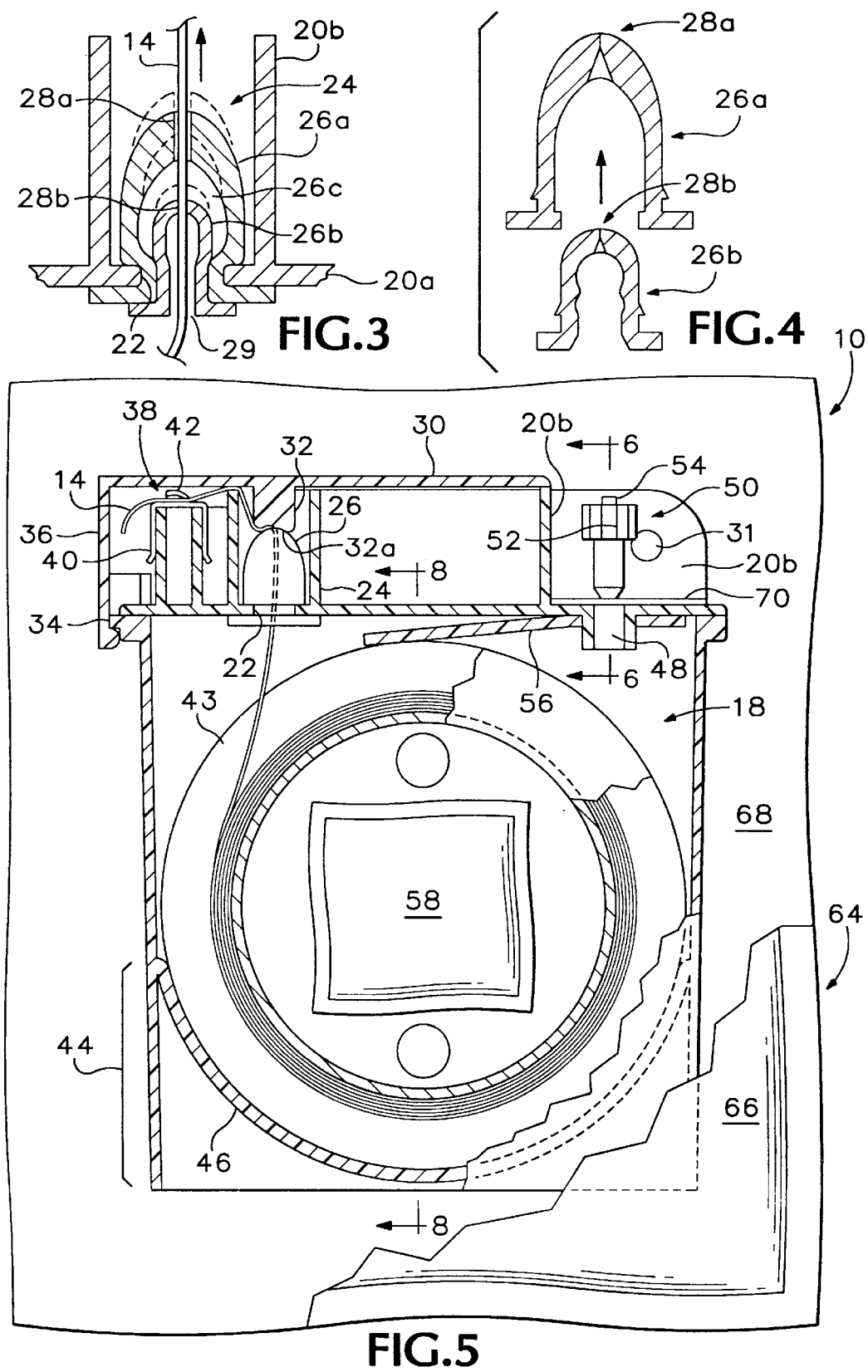

SUTURE-MATERIAL-DISPENSER SYSTEM FOR SUTURE MATERIAL

BACKGROUND AND SUMMARY OF THE INVENTION

The present invention relates generally to suture-material dispensers. More particularly, the invention concerns a novel suture-material-dispenser system for dry suture material in which the dry suture material is packaged with a desiccant. The disclosures of my prior filed U.S. Pat. applications Ser. Nos. 08/175,964 and 08/497,432 are incorporated herein by reference.

Generally speaking, the present invention is usable for all surgical applications, but it is particularly suited for use by veterinary surgeons, as will be better understood from the description below. For that reason, the present invention will be described in the context of use by veterinary surgeons. As used below, the word sterile or sterilization means that degree of sterility which is found acceptable in veterinary surgery.

Conventional suture dispensers are well known. Such dispensers are characterized by having relatively large dimensions, and are constructed for holding wet suture material, one type of conventional suture material that is packaged in an alcohol-based solution. The other type is dry suture material and it will be discussed below in connection with the present invention.

To sterilize wet suture material in conventional, so-called "wet-pack" dispensers, an extreme procedure must be followed which involves irradiating the filled dispenser with gamma-ray radiation. Such a procedure is extreme because it tends to modify or adversely affect the molecular structure of the suture material. After irradiation, suture material from conventional "wet packs" tends to become weaker and stiffer, which makes it more difficult for a surgeon to work with. The integrity of the material is also compromised. Such an extreme sterilization procedure is required because there is no other known way to sterilize wet suture material.

Conventional dispensers, or "wet packs", are also disfavored because the wet suture material is messy, relatively heavy and flammable.

Conventional dispensers also require a two-handed operation for dispensing and cutting suture material. Essentially, the user, such as a surgeon or other surgical health care professional, holds the dispenser while removing a desired amount of suture material from the supply contained within the dispenser. Next, the user grasps a cutting instrument such as a pair of scissors and cuts the desired amount from the supply.

None of the conventional dispensers is designed for one-handed dispensing and cutting operation, and none is constructed for holding dry suture material.

In brief summary, one embodiment of the invention includes a suture-material-dispenser system for a supply of dry suture material with a housing and a gas-permeable, resilient member. The housing defines a cavity for containing a supply of such material, and it includes a top region that has an opening formed in it. The gas-permeable, resilient member has a body that fits sealingly within the opening, and the body has formed in it a suture-material-dispensing port for allowing suture material to be dispensed therethrough. The port is preferably formed as a slit with a length of about 2–6 mm.

The body assumes a pre-dispense condition and a dispense condition, and the body is formed from a substance with a memory characteristic allowing that section of the body adjacent the port to deform when the body is in the dispense condition, thus to minimize degradation of suture material during dispensing operation. The memory characteristic also allows the body to return substantially to its undeformed state when the body is in its pre-dispense condition, thus to seal substantially the cavity from contaminant.

The invention preferably also includes the following other features. An anti-contaminant, flip-top cover is pivotably attached to the top region, and is constructed for releasable closure over the top region substantially to prevent contaminants from entering the cavity. The cover also includes a downwardly extending, elongate pressure applicator with a bottom surface that presses against the resilient member adjacent the port when the cover is closed over the top region. The top region also includes a lip that extends outwardly from the housing, and the cover includes a downwardly extending expanse that is engageable with the lip to obtain such releasable closure.

An on-board cutter preferably is attached to the housing adjacent the resilient member for allowing the user to cut a desired dispensed amount of material from such supply. The resilient member preferably is formed from a material such as liquid-injection-molded silicone, which material is ethylene-oxide-gas permeable, and has the above-described memory characteristic. The resilient member also preferably is formed from a material with a hardness in the range of about 40–80 on a Shore A durometer.

Another aspect of the invention includes the above suture-material-dispenser system and the supply of dry suture material. That version of the invention also includes a reel fittable within the cavity, and having wound on it the supply. The housing also includes a bottom region and a semi-circular bearing positioned in the bottom region for supporting the reel. The reel includes a region for receiving desiccant to protect the suture material from excess moisture.

The advantages of the invention will be more clearly understood from a consideration of the accompanying drawings and the following description of the preferred embodiment.

BRIEF DESCRIPTION OF THE DRAWINGS

FIG. 3 is an enlarged, fragmentary, cross-sectional view through line 3—3 of FIG. 1, showing in an exaggerated way how the resilient member of the present invention deforms during dispensing, in dashed lines.

FIG. 4 is an enlarged, cross-sectional view the components of the resilient member shown in FIG. 3.

FIG. 5 is a side view of the system shown in FIG. 1 after the cover is moved to a closed position, shown enclosed in a sealed envelope as part of a sterilization and drying procedure, with parts of the envelope and system cut away to expose details of the system.

DETAILED DESCRIPTION OF THE PREFERRED EMBODIMENT

Figure 2:
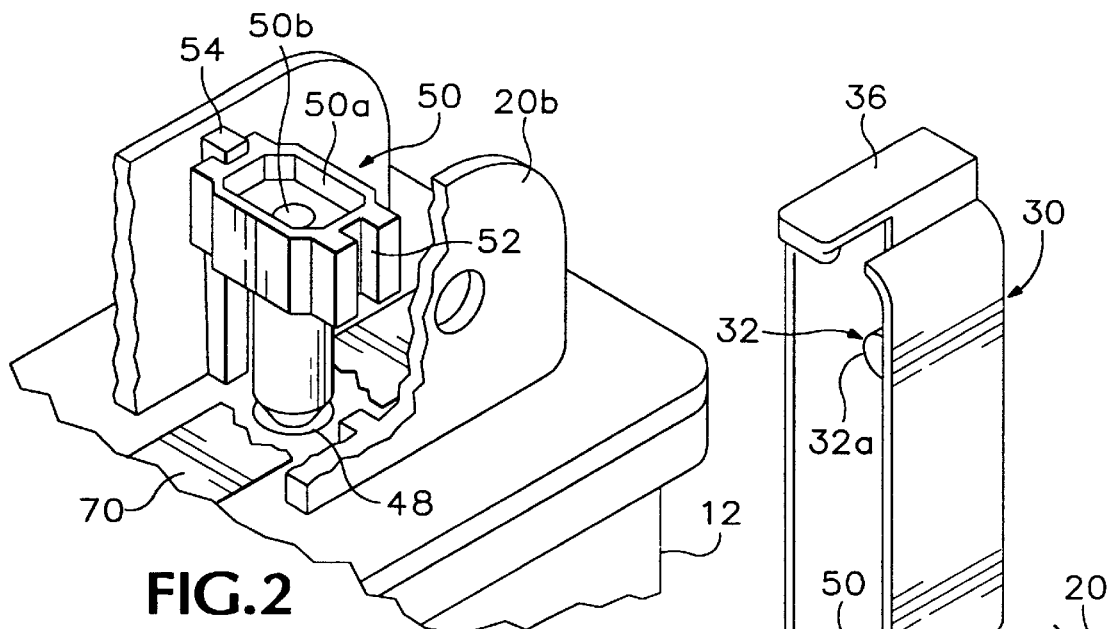
FIG. 2 is an enlarged, fragmentary, view of a top section of the system shown in FIG. 1 which illustrates a sealable opening and sealing plug of the invention.
Figure 1:
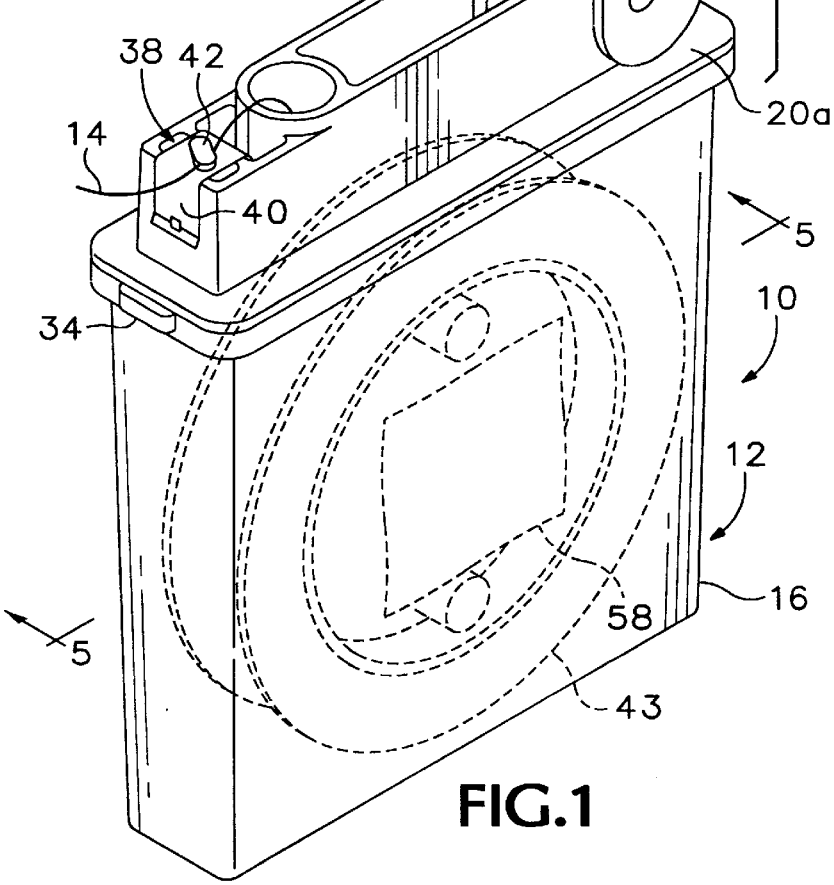
FIG. 1 is an isometric view showing the preferred embodiment of the suture dispenser system of the present invention with dry suture material stored on a spool, with a package of desiccant contained within the spool, and a cover of the dispenser system being pivoted to an open position allowing access to dry suture material contained in the system.
Figure 6:
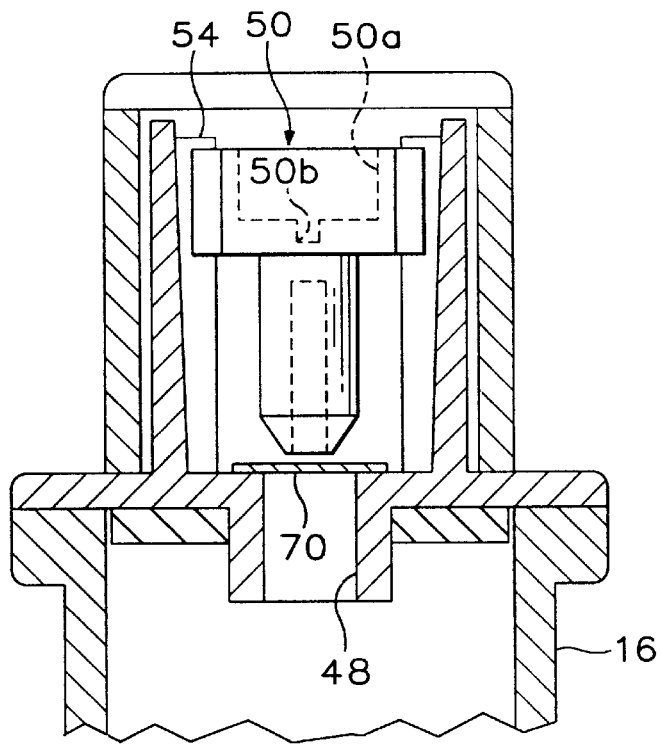
FIG. 6 is an end cross-sectional view of the sealable opening and sealing plug shown in FIG. 2, taken generally along line 6—6 in FIG. 5, shown with the plug in an open position.

FIG. 1 depicts an isometric view of the suture dispenser system of the present invention, being made in accordance with its preferred embodiment and indicated at 10. The preferred embodiment includes the to-be-described dispenser 12 and dry-suture material ("DSM") 14. DSM 14 can be obtained from CP Medical Of Portland, Oregon and suitable versions of DSM 14 are sold by CP Medical under the trademarks FLEX-GUT, MONOMID, and SUPRAMID. System 10 and the method described below are particularly well suited to synthetic absorbable sutures, such as those made of polyglycolic acid or polylactic acid, which must be stored with a moisture level in dispenser 12 of below 5-percent humidity.

Figures 9, 10:
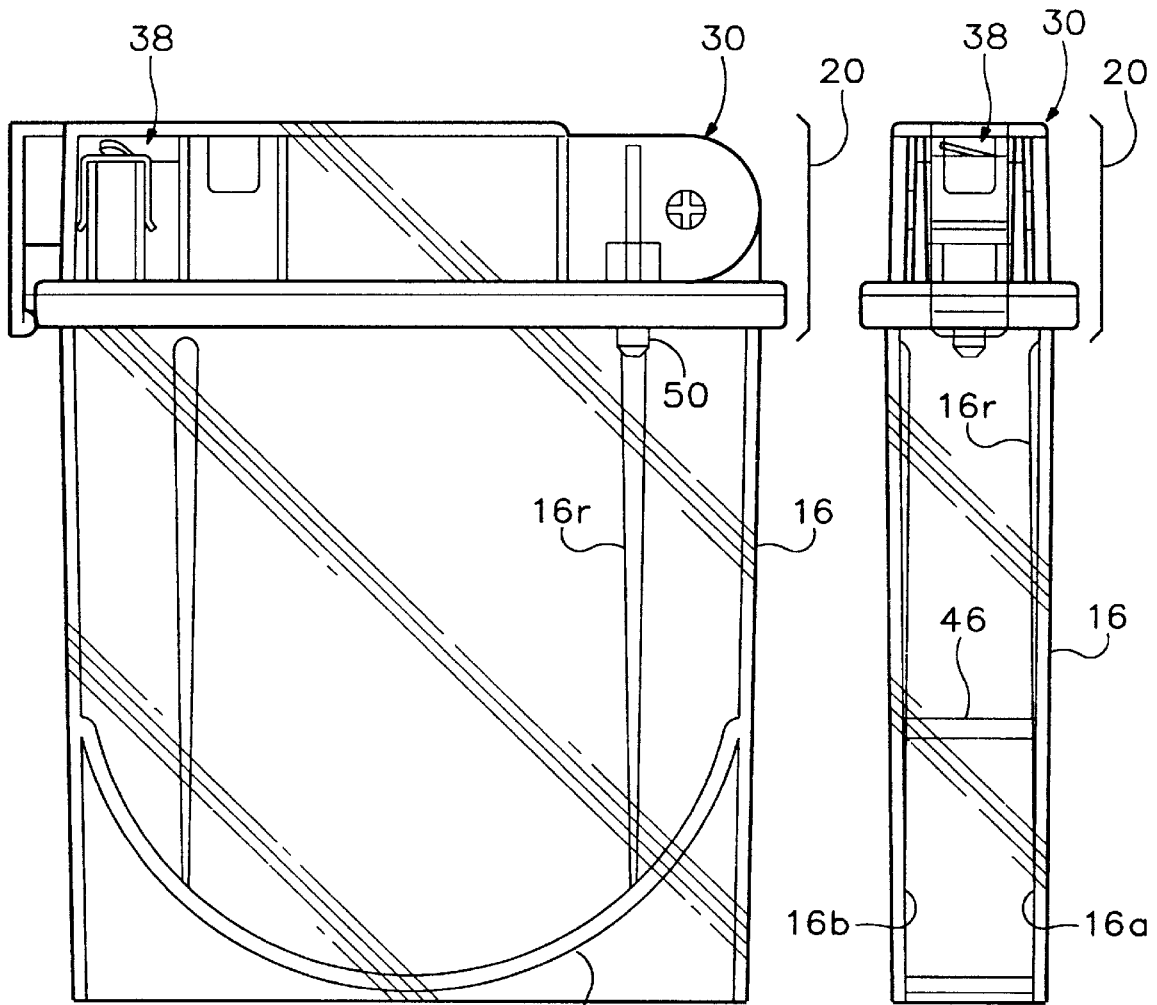
FIG. 9 is a side view of an alternative embodiment of the housing of the present invention, shown in approximately actual size.
FIG. 10 is an end view of the housing shown in FIG. 9, shown in approximately actual size.

Referring to FIGS. 1, 5, and 9, the invention includes a housing 16, preferably made from clear ABS plastic, which defines a cavity 18 (FIG. 5) for containing a supply of DSM 14. The overall dimensions of system 10 are about 4 5/16" high ×3 13/16" long ×7/8" wide. The housing includes opposing walls 16a–b (FIG. 9) and a top region 20 that has an opening 22 (FIG. 5) formed in it.

Top region 20 includes a plate-like member 20a which can be fastened to housing 16 using suitable means such as adhesive or sonic welding. All components of system 10 preferably are made of a suitable plastic, but any suitable material may be used. Top region 20 also includes a raised member 20b which is positioned fixedly and centrally of plate-like member 20a.

Referring to FIGS. 3 and 4, a gas-permeable, resilient member 24 fits sealingly within opening 22. Member 24 is shown preferably to include an outer body 26a that fits sealingly within opening 22, and an inner body 26b encased within outer body 26a by fitting sealingly within a hollow of outer body 26a. Bodies 26a and 26b are substantially self supporting, holding DSM 14 away from housing 16 as DSM 14 exits housing 16. An airlock or pocket 26c of trapped gas is defined between the upper portions of bodies 26a and 26b, as seen best in FIG. 3. Bodies 26a and 26b collectively define a very effective vapor barrier, protecting DSM 14 from damage by moist outside air. A suture-material-dispensing port 28a and 28b is formed in bodies 26a and 26b, respectively, for allowing DSM 14 to be dispensed through member 24.

Two conditions of bodies 26a and 26b are shown, a pre-dispense condition and a dispense condition. FIG. 3 shows a to-be-described memory characteristic of bodies 26a and 26b, in an enlarged and exaggerated way in dashed lines. The portions of bodies 26a and 26b adjacent port 28 deform when the body is in the dispense condition with DSM 14 being pulled out of cavity 18 in the direction of the arrow. Such deformation, combined with the to-be-described softness of bodies 26a and 26b, tends to minimize degradation of suture material during dispensing operations.

With respect to material choice for bodies 26a and 26b, the preferred material is liquid-injection-molded, or LIM, silicone. The material also has a hardness in the range of about 40–80 on a Shore A durometer. The material is also preferably ethylene-oxide-gas permeable to allow system 10 to be sterilized according to a to-be-described, ethylene-oxide-gas sterilization procedure. Alternatively, bodies 26a and 26b may be made of natural rubber.

Referring back to FIG. 3, the memory characteristic of bodies 26a and 26b allows the body to return substantially to its undeformed state when the body is in its pre-dispense condition as shown in solid lines. The pre-dispense condition occurs when no dispensing, or pulling, force is applied to DSM 14. By returning to its undeformed state, bodies 26a and 26b will seal substantially cavity 18 (FIG. 5) from contaminant.

Preferably, port 28 is formed as a conical depression in body 26 with a slit formed in bodies 26a and 26b as DSM is fed through bodies 26a and 26b to maximize the capability of bodies 26a and 26b to seal cavity 18 from contaminant. Bodies 26a and 26b are shown in FIG. 3 also with a cylindrical void 29 which communicates with port 28 and cavity 18. The shape of that void is not critical however, and bodies 26a and 26b could also be constructed substantially hollow with only a suitable uniform thickness associated with its surface area.

Referring to FIGS. 1 and 5, system 10 also preferably includes an anti-contaminant, flip-top cover 30 which is attached pivotably to top region 20 via opposing bosses 31 which extend inwardly from opposing sides of the cover into suitable, corresponding holes formed in top region 20. Cover 30 is constructed for releasable closure over the top region substantially to prevent contaminants from entering the cavity. In this way cover 30 acts as a backup seal to the primary seal provided by bodies 26a and 26b as described above in connection with FIG. 3.

Still referring to FIGS. 1 and 5, cover 30 includes a downwardly extending, elongate pressure applicator 32 with a bottom surface 32a that presses against resilient member 24 adjacent port 28 when cover 30 is closed over top region 20. Pressure applicator 32 functions as another backup seal by covering the top surface area of outer body 26a around port 28.

To provide releasable closure of cover 30 over top region 20, top region 20 is preferably constructed with a lip 34 that extends outwardly from housing 16, and cover 30 includes a downwardly extending expanse 36 that is engageable with lip 34 to obtain such releasable closure.

Referring to FIGS. 1 and 5, system 10 also preferably includes an on-board cutter 38 attached to raised member 20b of top region 20 of housing 16 adjacent resilient member 24. Cutter 38 allows the user to cut a desired dispensed amount of DSM 14 from the remaining supply of that material in cavity 18. Cutter 38 preferably is made as an elongate section 40 of a suitable metal. Section 40 is die cut to form a cutter blade 42 which is bent upwardly a suitable amount to allow DSM 14 to be fed under it and, ultimately, pulled against it to cut a desired amount of DSM 14 from the supply. Section 40 is formed as a clip to fit over a section of raised member 20b, but any suitable means of attaching cutter 38 to dispenser 12 may of course be used.

Referring to FIG. 5, system 10 also preferably includes a reel 43 fittable within cavity 18 for retaining the supply of DSM 14. To support reel 43, a bottom region 44 of housing 16 includes a semi-circular bearing 46 positioned in it. Given the below described dimensions of system 10, reel 43 is sized to hold between about 50–110 yards of DSM 14. Reel 43 preferably is made of a durable plastic material such as clear ABS plastic.

Referring to FIGS. 2 and 5–7, there is shown an auxiliary sealable opening 48 formed in top region 20 with a sealing plug 50 slidably engageable with opening 48. Sealing plug 50 preferably is made from polypropylene, and formed with grooves 52. Top region 20 of housing 16 is formed with rails 54 that may be gripped by grooves 52. Rails 54 are adjacent opening 48, and allow sealing plug 50 to be held adjacent opening 48 in an open position as shown in FIGS. 1, 2, 5 and 6, in which opening 48 is unobstructed. This allows gases to pass into and out of housing 16.

Figure 7:
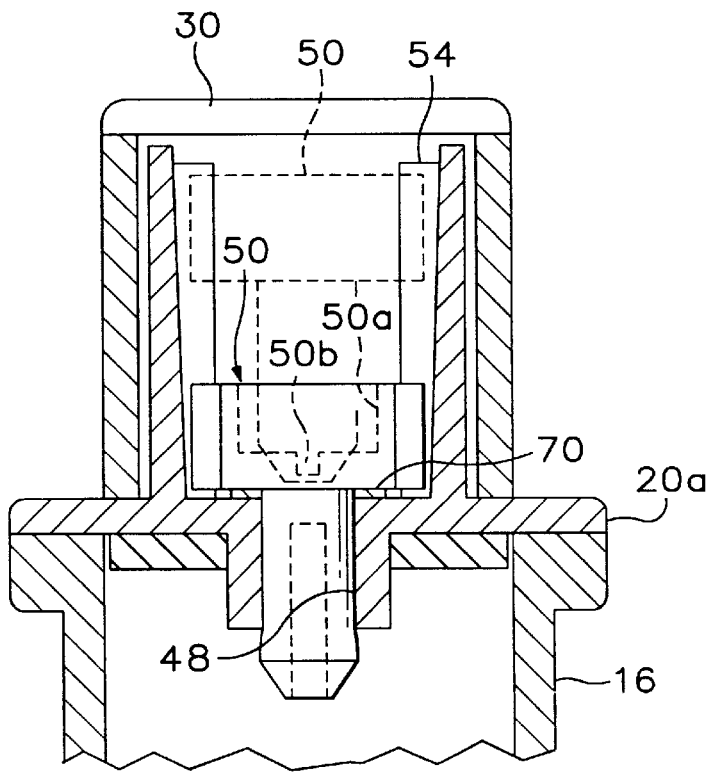
FIG. 7 is an end cross-sectional view of the sealable opening and sealing plug shown in FIG. 6, shown with the plug in a closed position.

Sealing plug 50 may be slid along rails 54 from the open position to a closed position as shown in FIGS. 7 and 9, in which plug 50 obstructs opening 48. If this sliding is performed by a machine, a depression 50a (FIG. 2), including a hole 50b may be formed in plug 50, and the machine (not shown) may be formed with a matching protrusion and stub to mate with depression 50a and hole 50b, respectively. This helps to keep plug 50 lined up with opening 48 as plug 50 is slid along rails 54.

A spring-biased support plate 56 also is attached to the underside of plate-like member 20a, as shown in FIG. 5.

Figure 8:
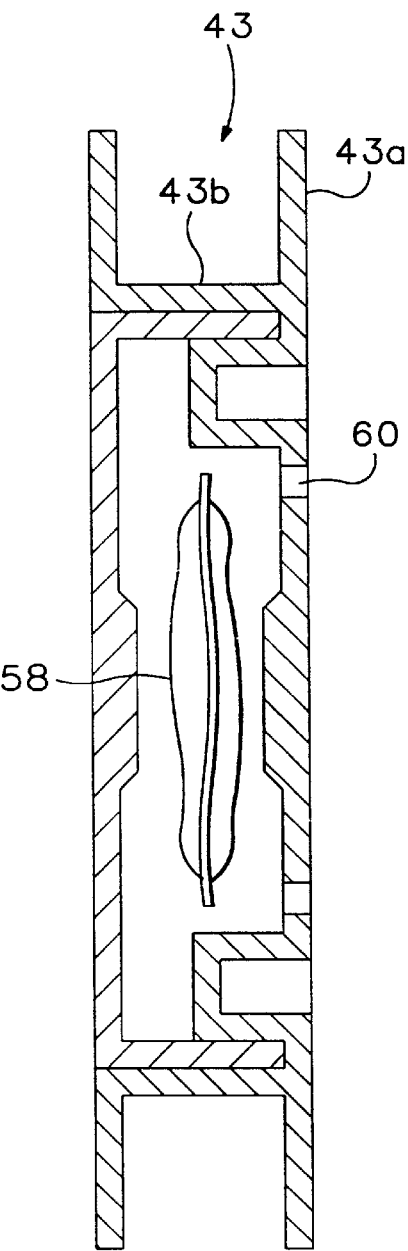
FIG. 8 is a side cross-sectional view of an alternative embodiment of the reel shown in FIG. 5, taken along line 8—8 in FIG. 5, shown on a larger scale than in FIG. 5.

Central spool 43b may be any suitable size, and preferably spool 43b is sized to hold between about 50–110 yards of suture material. Preferably, disks 43a have a diameter of about 3 3/16", and spool 43b has a diameter of about 2 7/16". With the preferred diameters, spool 43b defines an open region of sufficient size to receive and hold desiccant material 58, as shown in FIGS. 1, 5 and 8. Reel 43 may be formed with an open side, as shown in FIGS. 1 and 5, or with enclosed sides, as shown in FIG. 8. If closed sides are included, one or more vent holes 60 may be provided so that desiccant material 58 may be in gaseous communication with suture material 14.

Desiccant material 58 is shown in the form of a packaged desiccant, but other forms of desiccant may be used, as desired. While it has been found that the packaged desiccant is handled easily and contained when placed within the open region of spool 43b as shown, it is possible to place desiccant material 58 in other locations within housing 16. For example, desiccant material 58 may be placed outside of dispenser 12, but within a sealed envelope 64.

Figure 11:
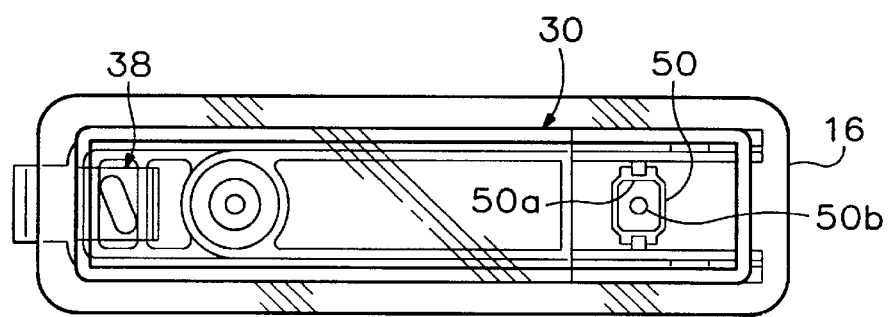
FIG. 11 is a top view of the housing shown in FIG. 9, shown in approximately actual size.

In FIGS. 9 through 11, an alternative embodiment of the housing is shown, identified generally at 16. Top region 20, flip-top cover 30, cutter 38, and semi-circular bearing 46 are labeled for reference, as appropriate. Ridges 16r extend inwardly from walls 16a and b to provide lines of bearing against reel 43. This has been found to improve the spinning characteristics of reel 43 within housing 16.

OPERATION

In use, system 10 can be held easily in the user's hand and stored in a pocket of the user's clothing. From its covered position as shown in FIG. 5, the user simply presses outwardly and upwardly against the bottom of expanse 36 (i.e. the bottom as shown in FIG. 5) to disengage it from lip 34 and open cover 30. When cover 30 is in its open position (FIG. 1), the user simply pulls a desired amount of DSM 14 from housing 16 and cuts that amount from the supply of DSM 14 by feeding under cutter blade 42 and then pulling that amount against that blade.

After dispensing, the user is able to close flip-top cover 30 with the same hand being used to hold system 10 by simply pushing down on an accessible section of the cover with the thumb. With respect to later use of the section of DSM 14 that extends outwardly from resilient member 24 to cutter 38 (see FIG. 5), it will depend on the user's own sterile procedures and the type of material. If sterile gloves are used when handling DSM 14, it is likely that that section is sufficiently sterile for use, provided that it has not degraded due to exposure to a moist environment, for example.

It should now be understood that the present invention provides a suture-material-dispenser system which overcomes the drawbacks of prior art systems. System 10 is constructed for holding and dispensing dry suture material, and for allowing that material to be sterilized using a substantially dry, gas sterilization procedures such as ethylene-oxide-gas sterilization. One such procedure is performed by Dravon Medical of Portland, Oregon. Either 100% ethylene oxide or 12% formaldehyde/88% ethylene oxide can be used to perform that gas sterilization.

These procedures may be modified in unique ways due to the novel structure of sealing plug 50 and top region 20. For example, system 10 may be enclosed in an envelope such as envelope 64 shown in FIG. 5. Envelope 64 may be made with a see-through or clear side 66 and with a gas-permeable side 68. Clear side 66 may be made of clear mylar, and gas-permeable side 68 may be made of Tyvek or other material that allows gasses to pass through the material, but prevents particulates and bacteria from passing through. Other forms of gas-permeable containers may be used in place of envelope 64, although few offer the simplicity and ease of use of envelope 64.

System 10, while enclosed in envelope 64, may be gas sterilized, with plug 50 in an open position to allow maximum gas flow within housing 16. The resulting sterilized package may then be dried within a sterile environment, preferably at 200-degrees Fahrenheit for 3 hours, under a vacuum. Prior to or immediately after removing system 10 and envelope 64 from the drier, but before removing system 10 from envelope 64, sealing plug 50 is moved to a closed position within auxiliary opening 48, sealing opening 48 to limit gas flow within housing 16.

The slidable or movable mounting of plug 50 to top 20 allows this sealing procedure to be performed manually or mechanically, without removing system 10 from envelope 64. Alternatively, this sealing procedure may be performed without use of opening 48 and plug 50, by sterilizing dispenser 10 prior to sonically welding top region 20 to housing 16. This is best done in a clean room environment, to avoid exposing DSM 14 to contaminants or humidity.

Alternative embodiments of system 10 could achieve the same result by including an auxiliary opening at other locations on system 10, and by using other means for movably connecting plug 50 to housing 16, or more generally to system 10. For example, opening 48 could be formed in walls 16a or 16b, or in bearing 46. Preferably, sealing plug 50 and rail 54 are protected by walls 20b extending outwardly from housing 16. This limits the chances that sealing plug 50 will be dislodged inadvertently from rail 54. Alternatively, plug 50 might be attached temporarily to envelope 64, not shown.

A further alternative includes covering sealable opening 48 with a gas-permeable material, such as a strip of Tyvek tape 70 placed over opening 48, as shown in FIG. 5, before creating the sterilized package and before sealing opening 48. When plug 50 is pushed through opening 48, it pierces or displaces tape 70. This further limits infiltration of cavity 18 by any contaminants during the handling and processing of dispenser 12 prior to and during the sterilization and drying procedures. Tape 70 could be any type of gas-permeable material, and could be applied to opening 48 by being located within opening 48 or within housing 16, as desired.

While the invention has been disclosed in its preferred form, it is to be understood that the specific embodiment thereof as disclosed and illustrated herein is not to be considered in a limiting sense. Numerous variations are possible and that no single feature, function, or property of the preferred embodiment is essential. The invention is to be defined only by the scope of the issued claims.

It is claimed and desired to secure by Letters Patent:

1. A suture-material-dispenser system having a suture-dispensing opening, the system comprising:

a housing having an auxiliary sealable opening;

suture material contained within the housing; and a sealing plug movably mounted relative to the housing so that the sealing plug may be held in an open position in which the auxiliary sealable opening is unobstructed, and so that the sealing plug may be moved from the open position to a closed position in which the sealing plug obstructs the auxiliary sealable opening.

2. The suture-material-dispenser system of claim 1, further comprising gas-permeable material covering the auxiliary sealable opening.

3. The suture-material-dispenser system of claim 2, wherein the gas-permeable material covering the auxiliary sealable opening is a tape applied to the auxiliary sealable opening.

4. The suture-material-dispenser system of claim 2, wherein the gas-permeable material covering the auxiliary sealable opening is located within the housing.

5. The suture-material-dispenser system of claim 4, wherein the gas-permeable material covering the auxiliary sealable opening is a tape.

6. The suture-material-dispenser system of claim 2, wherein the gas-permeable material covering the auxiliary sealable opening is located within the auxiliary sealable opening.

7. The suture-material-dispenser system of claim 1, further comprising a rail adjacent the axillary sealable opening, wherein:

the sealing plug includes a groove that grips the rail; and the sealing plug may be moved from the open position to the closed position by sliding the sealing plug along the rail.

8. The suture-material-dispenser system of claim 7, wherein the sealing plug and rail are protected by walls extending outwardly from the housing to limit the chances that the sealing plug will be dislodged inadvertently from the rail.

9. A suture-material-dispenser system for a supply of dry suture material, comprising:

a housing which defines a cavity for containing a supply of suture material, with the housing including an opening; and a resilient member having an outer body that fits sealingly within the opening, and an inner body that fits sealingly within the outer body, the outer body and inner body each having a suture-material-dispensing port for allowing suture material to be dispensed therethrough, each body having a pre-dispense condition and a dispense condition, and each body being formed from a substance with a memory characteristic that allows the body adjacent the port to deform when the body is in the dispense condition, thus to minimize degradation of suture material during dispensing of suture material, and the memory characteristic also allows the body to return substantially to the pre-dispense condition, thus to seal substantially the cavity from contaminant.

10. The suture-material-dispenser system of claim 9, wherein the outer body and inner body of the resilient member define a pocket of trapped gas therebetween.

11. The suture-material-dispenser system of claim 9, wherein the outer body and inner body of the resilient member define a pocket of trapped gas therebetween, located directly between the ports of the outer body and the inner body.

12. A suture-material-dispenser system, comprising:

a housing having an opening;

suture material contained within the housing; and a resilient member held within the opening of the housing, formed from an outer body with a suture-material-dispensing port and an interfitting inner body with a suture-material-dispensing port, wherein the outer body and inner body define a pocket of trapped gas therebetween.

13. The suture-material-dispenser system of claim 12, wherein the pocket of trapped gas is located directly between the ports of the outer body and the inner body.

14. A suture-material-dispenser system having a suture-dispensing opening, the system comprising:

a housing means for housing suture material;

an auxiliary opening means for allowing gas to pass into and out of the housing means; and a movable plug means for sealing the auxiliary opening means, the movable plug means movably mounted relative to the housing so that the plug means may be held in an open position in which the auxiliary opening means is unobstructed, and so that the plug means may be moved from the open position to a closed position in which the plug means obstructs the auxiliary opening means.

15. A suture-material-dispenser system, comprising:

a housing having a sealable opening;

suture material contained within the housing;

gas-permeable tape covering the sealable opening; and a sealing plug movably mounted relative to the housing so that the sealing plug may be held in an open position in which the sealable opening is unobstructed, and so that the sealing plug may be moved from the open position to a closed position in which the sealing plug obstructs the sealable opening.

16. A suture-material-dispenser system, comprising:

a housing having a sealable opening;

suture material contained within the housing;

gas permeable tape covering the sealable opening, the gas permeable tape being located within the housing; and a sealing plug movably mounted relative to the housing so that the sealing plug may be held in an open position in which the sealable opening is unobstructed, and so that the sealing plug may be moved from the open position to a closed position in which the sealing plug obstructs the sealable opening.

17. A suture-material-dispenser system, comprising:

a housing having a sealable opening;

suture material contained within the housing;

a rail adjacent the sealable opening; and a sealing plug movably mounted relative to the housing so that the sealing plug may be held in an open position in which the sealable opening is unobstructed, and so that the sealing plug may be moved from the open position to a closed position in which the sealing plug obstructs the sealable opening, wherein the sealing plug includes a groove that grips the rail, and wherein the sealing plug may be moved from the open position to the closed position by sliding the sealing plug along the rail.

18. The suture-material-dispenser system of claim 17, wherein the sealing plug and rail are protected by walls extending outwardly from the housing to limit the chances that the sealing plug will be dislodged inadvertently from the rail.

* * * * *